(12) United States Patent
Taguchi et al.

(10) Patent No.: US 7,534,332 B2
(45) Date of Patent: May 19, 2009

(54) GAS SENSOR MANUFACTURING PROCESS, AND GAS SENSOR

(75) Inventors: Masataka Taguchi, Kagamihara (JP); Yasuhiro Fujita, Kaizu (JP); Hiromichi Hayashi, Nagoya (JP)

(73) Assignee: NGK Spark Plug Co., Ltd., Aichi (JP)

( * ) Notice: Subject to any disclaimer, the term of this patent is extended or adjusted under 35 U.S.C. 154(b) by 732 days.

(21) Appl. No.: 11/073,587

(22) Filed: Mar. 8, 2005

(65) Prior Publication Data

US 2005/0198810 A1    Sep. 15, 2005

(30) Foreign Application Priority Data

Mar. 9, 2004    (JP) .................. P. 2004-066223

(51) Int. Cl.
    *G01N 27/417* (2006.01)
(52) U.S. Cl. ................ 204/428; 204/421; 204/423; 204/424; 73/23.31; 73/23.32
(58) Field of Classification Search ......... 204/421–432; 73/23.31–23.32
    See application file for complete search history.

(56) References Cited

U.S. PATENT DOCUMENTS

| | | | |
|---|---|---|---|
| 6,346,179 B1 | 2/2002 | Makino et al. | |
| 6,726,819 B2 | 4/2004 | Atsumi et al. | |
| 6,945,091 B2 * | 9/2005 | Nakagawa | 73/31.05 |
| 2002/0144538 A1 * | 10/2002 | Yamada et al. | 73/31.05 |

FOREIGN PATENT DOCUMENTS

| | | |
|---|---|---|
| DE | 23 51 815 A1 | 4/1975 |
| DE | 34 10 122 A1 | 10/1985 |
| JP | 9-304322 | 11/1997 |
| JP | 2000-28571 | 1/2000 |
| JP | 2001-99807 | 4/2001 |

OTHER PUBLICATIONS

German Office Action 10 2005 010 885.7-52 dated Sep. 18, 2007.

* cited by examiner

*Primary Examiner*—Kaj K Olsen
*Assistant Examiner*—Bach T Dinh
(74) *Attorney, Agent, or Firm*—Sughrue Mion, PLLC (57) ABSTRACT

A process for manufacturing a gas sensor, the gas sensor including a gas detecting element, cylindrical metal shell, and cylindrical protector as defined herein, the process comprising: applying a lubricant to an outer circumference of a leading end portion of the metal shell; assembling the metal shell having the lubricant applied thereto and the protector, so that a fitting portion, in which the leading end portion of the metal shell and the protector fit on each other, and a space-forming portion, in which the leading end portion of the metal shell and the protector overlap each other through an annular space, are formed along an axial direction; and welding the metal shell and the protector by forming a welded portion extending from an outer circumference of the protector through the annular space.

13 Claims, 6 Drawing Sheets

GAS SENSOR MANUFACTURING PROCESS, AND GAS SENSOR

BACKGROUND OF THE INVENTION

1. Field of the Invention

The present invention relates to a gas sensor and, more particularly, to a gas sensor provided with a protector for covering a portion of a bottomed cylindrical or plate-shaped gas detecting element that is exposed to a gas to be measured.

2. Description of the Related Art

When the air/fuel ratio of an automobile is to be controlled, a gas sensor provided with a gas detecting element having electric characteristics varying with the concentration of a specific gas component in the exhaust gas is conventionally used. A variety of sensors such as an oxygen sensor, a NOx sensor or an HC sensor are known. In this gas sensor, the gas detecting element is held in a metal shell such that its leading end portion protrudes therefrom. The specific gas component (e.g., oxygen) in the gas to be measured such as the exhaust gas is detected by exposing the leading end portion of the gas detecting element to the measured gas.

In most gas sensors, moreover, a metallic protector for covering the leading end portion is mounted on the metal shell so that the leading end portion of the gas detecting element to be exposed to the measured gas is protected from contact with water. This protector has a plurality of gas communication holes, through which the measured gas is introduced into the protector and contacts the leading end portion of the gas detecting element. In order to enhance protection of the leading end portion of the gas detecting element, moreover, the protector most frequently used in recent years has employed a dual structure composed of two members, namely an inner cover portion and an outer cover portion. A gas sensor having such a protector is disclosed in JP-A-9-304332, JP-A-2000-28571 and JP-A-2001-99807, for example.

3. Problems to be Solved by the Invention

Various methods have been adopted for fixing the protector and the metal shell. In order to fix these two components reliably, a method has also been frequently adopted in which a cylindrical protector is fitted on the radially outer side of the leading end portion of the metal shell and in which a welded portion (e.g., a laser welded portion) is formed for the fitting portion. In case the protector is to be fitted on the leading end portion of the metal shell, a lubricant is applied to the surface of the metal shell. As such, the fitting between the inner circumference of the protector and the outer circumference of the leading end portion of the metal shell may be smoothed by reducing friction therebetween, to thereby fit the protector by means of the lubricating action of the lubricant. In mass production of the sensor, the lubricant is ordinarily applied to the whole surface of the metal shell. When the protector is to be fitted on the leading end portion of the metal shell, press-fitting ordinarily is also adopted so as to ensure a fitting relation.

If, however, the fitting portion, in which the protector is fitted by applying the lubricant to the surface of the metal shell, is welded (or lap-welded), the gas of the lubricant component resulting from heat input of the welding operation has no clear avenue of release, thereby causing a welding defect such as a blow hole. It is, therefore, conceivable to selectively remove, after applying lubricant to the surface of the metal shell, that lubricant on the portion of the metal shell which is to form the welded portion. However, such selective removal requires much step management, thus raising problems of lowered manufacturing efficiency and increased cost.

SUMMARY OF THE INVENTION

The invention has been conceived with the aim of solving the above problems of the prior art, and an object thereof is to provide a gas sensor manufacturing process, which is free from welding defects such as a blow hole, even when a protector is press-fitted in a metal shell having a lubricant applied to its surface and a welded portion is then formed, and which contributes to an improvement in manufacture efficiency by eliminating special treatments such as selective lubricant removal.

Another object of the invention is to provide a gas sensor having a stable welded portion formed to firmly fix the protector and the metal shell.

The above-specified objects of the invention have been achieved by providing a process for manufacturing a gas sensor including:

a gas detecting element extending in an axial direction and having a leading end side which is to be exposed to a gas to be measured;

a cylindrical metal shell housing the radially outer side of the gas detecting element such that the gas detecting element protrudes from a leading end side of the metal shell, and a cylindrical protector mounted on the outer circumference of the leading end portion of the metal shell and covering the leading end side of the gas detecting element, the process comprising;

a preparing step of preparing the metal shell, to which a lubricant is applied to the outer circumference of the leading end portion;

an assembling step of assembling the metal shell having the lubricant applied thereto and the protector, so that a fitting portion, in which the leading end portion of the metal shell and the protector fit on each other, and a space-forming portion, in which the leading end portion of the metal shell and the protector overlap each other through an annular space, may be formed along the axial direction; and a welding step of welding the metal shell and the protector by forming a welded portion extending from the outer circumference of the protector through the annular space.

In the gas sensor manufacturing process of the invention, with the lubricant being applied to the outer circumference of the leading end portion of the metal shell, the assembling step of assembling the protector and the specific portion of the leading end portion of the metal shell by fitting the former on the latter, and the welding step of welding the metal shell and the protector, are sequentially carried out.

Here, the assembling step in the gas sensor manufacturing process of the invention forms the fitting portion, in which the leading end portion of the metal shell and the protector fit on each other, and the space forming portion, in which the leading end portion of the metal shell and the protector overlap each other through an annular space, along the axial direction. The welding step subsequent to the assembling step forms the welded portion extending from the outer circumference of the protector through the annular space.

Thus, an annular space is intentionally formed between the metal shell and the protector, and the welded portion is formed through the annular space. Even if lubricant remains on the leading end portion of the metal shell at the welding step, the gas of the gasified lubricant component can be released through the annular space from the trailing end side or the leading end side of the protector. According to the gas sensor manufacturing process of the invention, therefore, even when lubricant is applied to the whole surface of the metal shell, a satisfactory welded portion can be formed without any special treatment to selectively remove lubricant from that portion which is scheduled to have the welded portion. Another advantage of the invention is that it is thereby possible to improve the manufacturing efficiency and the yield of the gas sensor. According to the gas sensor manufacturing process of the invention, moreover, positioning by fitting and welding are made stably compatible to firmly fix the protector and the metal shell and thereby to provide a high quality gas sensor.

Here, the aforementioned preparing step prepares the metal shell, in which lubricant is applied to the outer circumference of at least the leading end portion. It is sufficient to apply a predetermined (or aimed) amount of lubricant to the surface of the metal shell, which has been formed to a predetermined shape, but the applying method is not particularly limited. For example, the metal shell for the gas sensor is formed into a predetermined shape by a machining method (e.g., plastic working, cutting working or grinding working). The lubricant (e.g., the lubricating, cutting or grinding oil), which has been employed at working for lubricating or cooling purposes, may be left as a residual lubricant. It is, therefore, sufficient to reduce the residual lubricant or add a new lubricant so that a predetermined amount of lubricant may be finally applied to the surface of the metal shell carrying the residual lubricant. Alternatively, it is sufficient to apply a predetermined amount of lubricant to the surface of the metal shell after the residual lubricant is entirely removed from the metal shell by degreasing or rinsing the metal shell.

The welded portion at the welding step is preferably formed using a high-density energy beam, such as laser welding, plasma welding or an electron beam welding method. Of these, laser welding is most preferably used in view of manufacturing efficiency or when manufacturing cost is taken into consideration. Moreover, the welded portion may be either an entire-circumference welded portion formed continuously over the entire circumference or may comprise spot-welded portions formed intermittently in the circumferential direction. However, an entire-circumference welded portion is preferred for achieving high welding strength between the protector and the metal shell.

In the invention, moreover, the protector to be mounted on the metal shell for covering the leading end side of the gas detecting element is not limited to a single structure but may comprise a plural-structure composed of two or more cylindrical members. For example, the protector may have a dual structure, which is composed of the outer cover portion and the inner cover portion arranged on the inner side of the outer side cover portion. In this dual structure, these cover portions may be mounted on the outer circumference of the leading end side of the metal shell with their trailing end portions overlapping each other, and the leading end portion of the metal shell and the two covers may be integrally welded together. In an alternative structure, the protector has a dual structure of an outer cover portion and an inner cover portion. With the outer cover portion and the inner cover portion being fixed in advance at either the outer cover portion or the inner cover portion, only one cover is mounted on the outer circumference of the leading end portion of the metal shell. In this case, the leading end portion of the metal shell and either cover are integrally welded.

In the gas sensor manufacturing process in accordance with the invention, the annular space preferably has a width in a radial direction of 0.03 mm or more The width of the annular space in a radial direction is preferably set to 0.03 mm or more so that a satisfactory degasifying effect can be obtained to form the stable welded portion. If the width of the annular space is less than 0.03 mm, the degasifying effect may be insufficient. Here, the upper limit of the width of the annular space may be suitably set to 0.1 mm or less so as to cause no burn-through of the molten metal during welding, while taking into consideration the material of the metal shell or the protector and the thickness of the protector.

In any of the gas sensor manufacturing processes in accordance with the invention, moreover, the leading end portion of the metal shell may include a larger-diameter portion and a smaller-diameter portion having a smaller external diameter than that of the larger-diameter portion. Also, the fitting portion may be formed by fitting the larger-diameter portion and the protector, whereas the space-forming portion is formed by overlapping the smaller-diameter portion and the protector through the annular space.

In the invention, at the leading end portion which is to receive the mounted protector, the metal shell is prepared in advance, which includes the larger-diameter portion and the smaller-diameter portion having a smaller external diameter than that of the larger-diameter portion. At the assembling step, moreover, the protector is fitted on the larger-diameter portion of the metal shell to form the annular space between the outer circumference of the smaller-diameter portion of the metal shell and the inner circumference of the protector, so that the aforementioned fitting portion and the aforementioned space-forming portion can be easily formed.

In any of the gas sensor manufacturing processes in accordance with the invention, moreover, the portion of the protector that is mounted on the outer circumference of the leading end portion of the metal shell may include a smaller-diameter portion and a larger-diameter portion having a larger internal diameter than that of the smaller-diameter portion. Also, the fitting portion may be formed by fitting the smaller-diameter portion and the leading end portion of the metal shell, whereas the space-forming portion is formed by overlapping the larger-diameter portion and the leading end portion of the metal shell.

In the invention, at the portion scheduled to be mounted on the leading end portion of the metal shell, a protector is prepared, which includes the smaller-diameter portion and the larger-diameter portion having a larger internal diameter than that of the smaller-diameter portion. At the assembling step, moreover, the smaller-diameter portion of the protector is fitted on the leading end portion of the metal shell such that the annular space may be formed between the inner circumference of the larger-diameter portion of the protector and the outer circumference of the leading end portion of the metal shell. As a result, the aforementioned fitting portion and the aforementioned space-forming portion can be easily formed.

In any of the gas sensor manufacturing processes in accordance with the invention, moreover, the fitting portion may have a length of 0.8 mm or more in the axial direction.

By setting the fitting portion, in which the protector and the leading end portion of the metal shell fit on each other, to a length of 0.8 mm or more, at the assembling step, it is possible to position and fix the protector with respect to the leading end portion of the metal shell, to thereby prevent the protector from moving off or coming out from the metal shell at the time of transferring to the welding step. Here, no particular restriction is made on the upper limit of the length of the fitting portion in the axial direction.

In any of the gas sensor manufacturing processes in accordance with the invention, moreover, the fitting portion may be formed by press-fitting the protector on the leading end portion of the metal shell. The fitting portion is formed by press-fitting the leading end portion of the metal shell and the protector so that the fixing strength between the metal shell and the protector can be made sufficiently strong at the assembling step.

In any of the gas sensor manufacturing processes in accordance with the invention, moreover, at least one recess is formed radially inward in the surface of the larger-diameter portion of the metal shell and made continuous from the leading end edge to the trailing end edge of the larger-diameter portion.

By using the metal shell, in which at least one of the recesses is formed in the larger-diameter portion, when the welded portion extending through the annular space between the smaller-diameter portion of the metal shell and the protector is to be formed, the gas of the gasified lubricant component can be released to the outside through the annular space and through the recesses. As a result, a more reliable degasifying effect can be obtained at the welding step to thereby suppress the formation of welding defects such as a blow hole more reliably. Here, the recesses may be formed either at the metal shell forming time or by knurling the shaped metal shell.

Also, according to the invention, a gas sensor is provided comprising: a gas detecting element extending in an axial direction and having a leading end side exposed to a gas to be measured; a cylindrical metal shell housing the gas detecting element such that the gas detecting element protrudes from the leading end side of the metal shell; and a cylindrical protector mounted on the outer circumference of the leading end portion of the metal shell and covering the leading end side of the gas detecting element, wherein the gas sensor has: a fitting portion, in which the leading end portion of the metal shell and the protector fit on each other; a space-forming portion, in which the leading end portion of the metal shell and the protector overlap each other through an annular space; and a weld portion welding said protector to said metal shell through said annular space.

The gas sensor of the invention is provided, as viewed from the mounting portion of the leading end portion of the metal shell and the cylindrical protector, with the fitting portion, in which the two fit on each other, and the space-forming portion, in which the two overlap through the annular space. Moreover, it should be noted that the protector is welded to the metal shell by the welded portion formed through the annular space interposed between the protector and the leading end portion of the metal shell. As a result, the gas sensor of the invention can be efficiently manufactured by the method thus far described, so as to have high-quality characteristics, in which a stable welded portion is formed and in which the protector and the metal shell are firmly fixed. From the viewpoint of retaining the water-proofing properties between the outer circumference of the leading end portion of the metal shell and the inner circumference of the protector, the welded portion is preferably formed over the entire circumference.

DETAILED DESCRIPTION OF THE INVENTION

Embodiments of the invention are described as follows with reference to the accompanying drawings. However, the present invention should not be construed as being limited thereto.

FIRST EMBODIMENT

Figure 1:
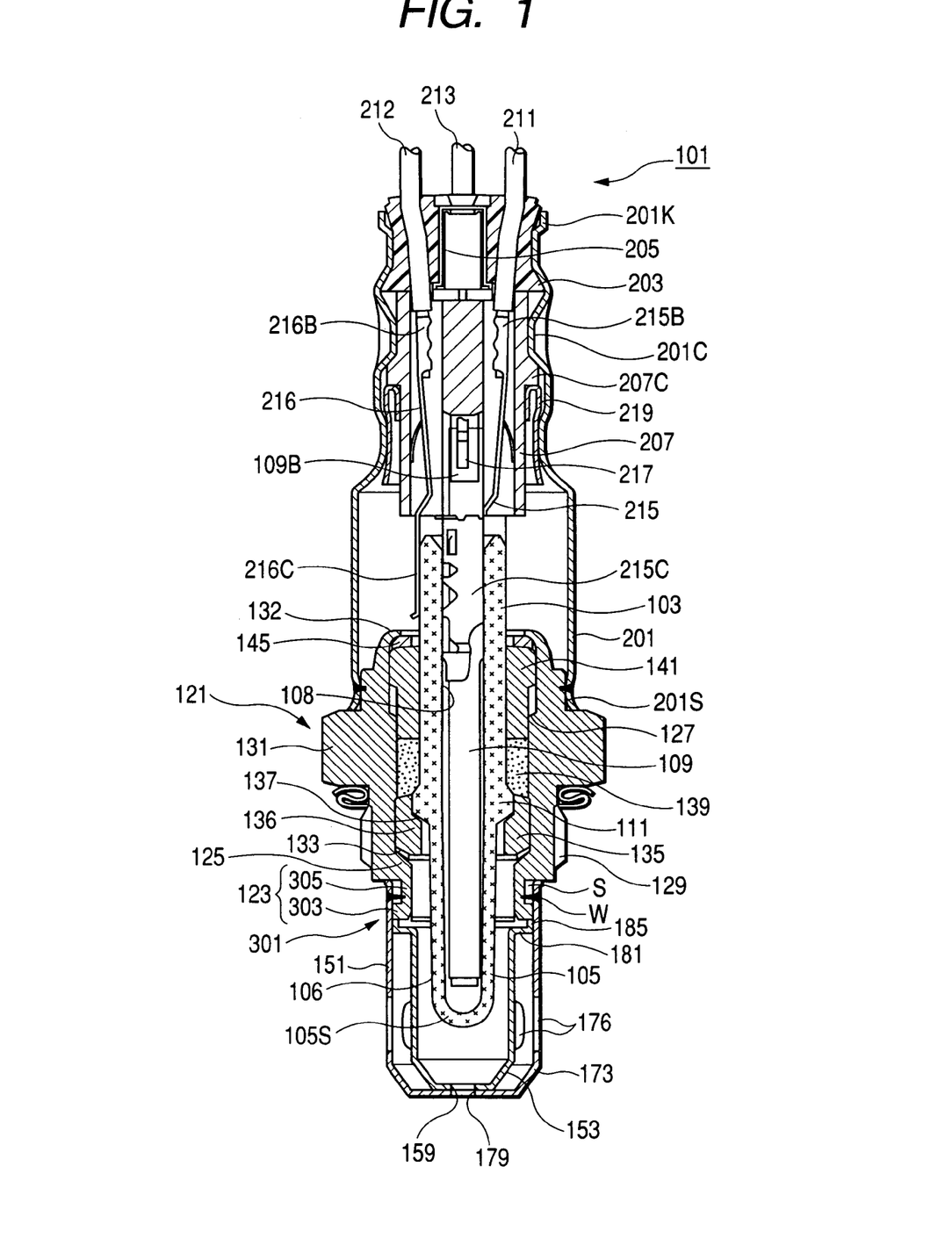
FIG. 1 is a sectional view of the entirety of a gas sensor according to an embodiment of the invention.
Figure 2:
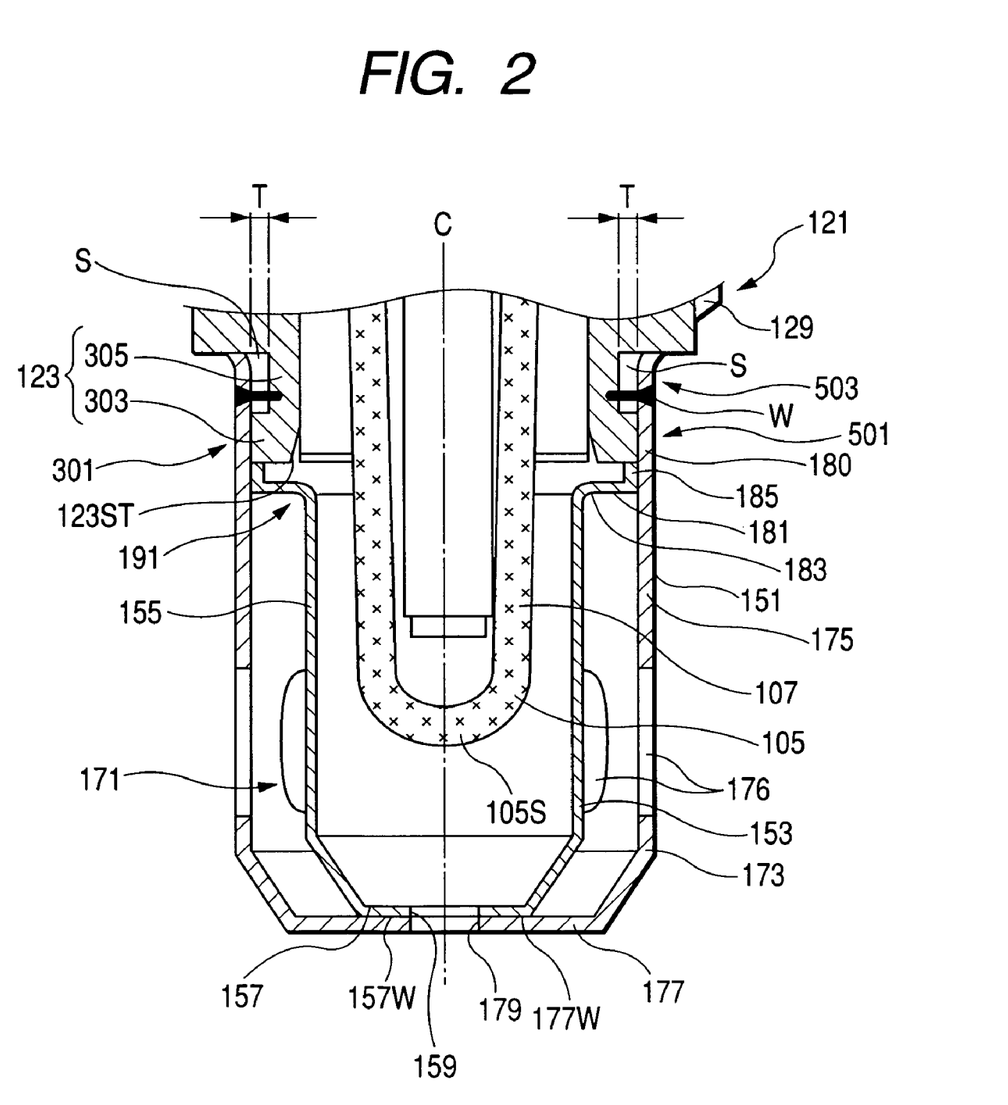
FIG. 2 is a sectional view showing a fixing structure between a protector and a metal shell according to the embodiment.
Figure 3:
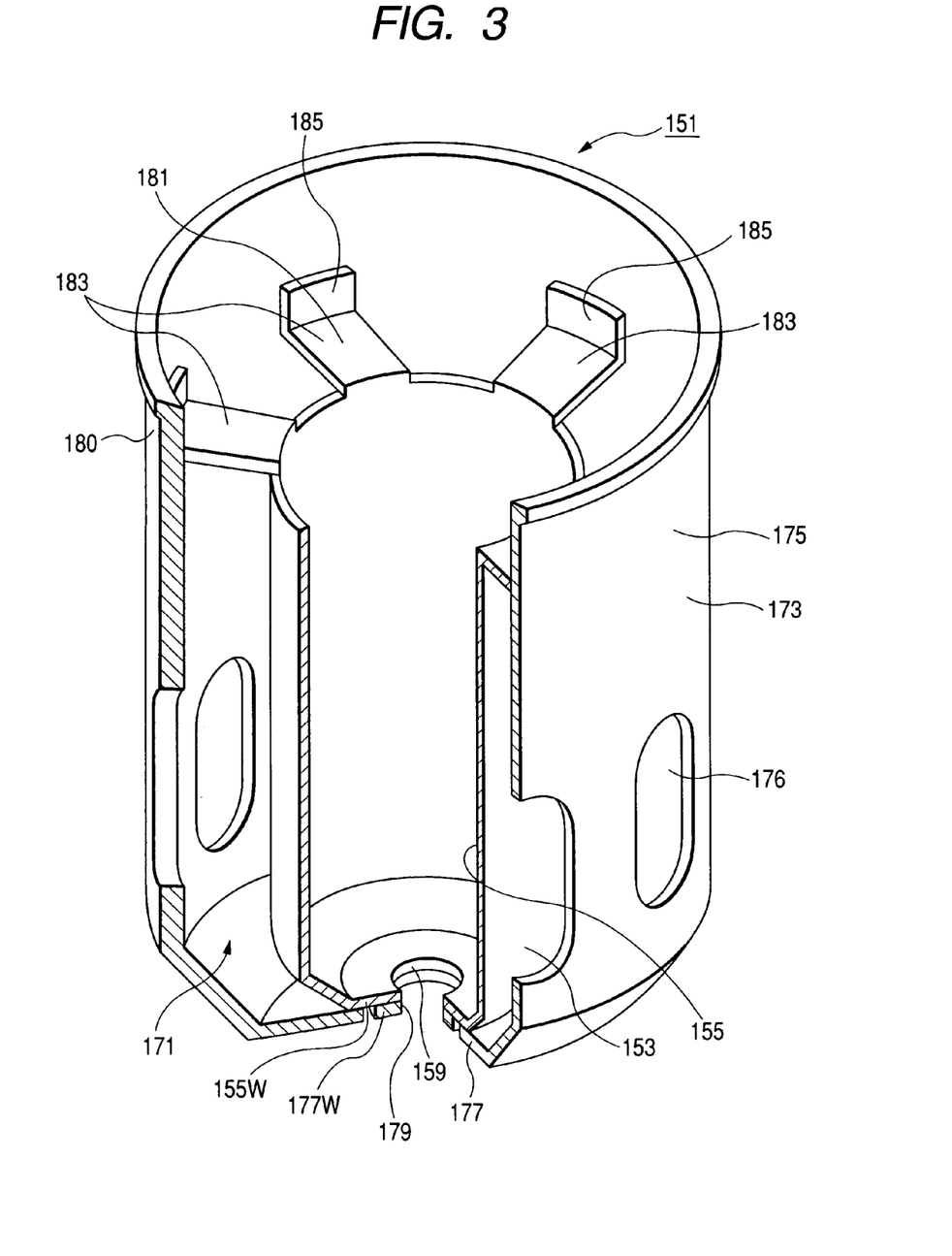
FIG. 3 is an explanatory view showing a protector having a dual structure in the gas sensor according to the embodiment.

A gas sensor 101 according to this embodiment is shown in section in FIG. 1 and a fixing structure between the protector and metal shell is shown in section in FIG. 2. An explanatory diagram showing a protector 151 is shown in FIG. 3. In FIG. 1 to FIG. 3, the lower portion is located on the leading end side, and the upper portion is located on the trailing end side. This gas sensor 101 is an oxygen sensor, which is attached to the exhaust gas pipe of an internal combustion engine for detecting the oxygen concentration in the exhaust gas to be measured. As shown in FIG. 1 and FIG. 2, the gas sensor 101 is provided with: a gas detecting element 103 extending in the direction of an axis C; a metal shell 121 having a cylindrical shape housing the gas detecting element 103; and the protector 151 for covering the leading end portion 105 of the gas detecting element 103 which is to be exposed to the exhaust gas.

Of these elements, the gas detecting element 103 is formed into a bottomed cylindrical shape having its leading end 105S closed, and is made mainly of partially stabilized zirconia containing a solid solution of yttria as a stabilizer. On the inner circumference of the gas detecting element 103, an internal electrode layer 108 is formed, which is made of porous Pt or a Pt alloy substantially covering the entire gas detecting element 103. A similar porous external electrode layer 106 is also formed on the outer circumference of the gas detecting element 103. This gas detecting element 103 is provided generally at its axially intermediate portion with an engaging flange portion 111, which protrudes radially outward. This engaging flange portion 111 is utilized for holding the gas detecting element 103 in the metal shell 121, as will be described hereinafter. Into the inner side of the gas detecting element 103, moreover, a ceramic heater 109 is inserted, which is formed in a rod shape and which has a heating resistor in its inner side.

The metal shell 121 is formed of SUS 430 into a cylindrical shape having a leading end portion 123 to be inserted into the protector 151. Moreover, the metal shell 121 is provided on its inner circumference with a shelf portion (or a support face) 125, which is positioned on the trailing end side of the leading end portion 123 for holding the gas detecting element 103 in the direction of the axis C. Moreover, a stepped portion 127 is formed on the trailing end side of the shelf portion 125. On the other hand, the metal shell 121 is provided, on its outer circumference and at a position on the trailing end side of the leading end portion 123, with a mounting thread 129 for mounting the gas sensor 101 on the exhaust gas pipe. The metal shell 121 is further provided, on the trailing end side of the mounting thread 129, with a hexagonal flange portion 131 (or a tool engaging portion), which is utilized when the gas sensor 101 is mounted on the exhaust gas pipe.

The leading end portion 123 of the metal shell 121 is the portion, which is to be inserted into the protector 151, as described hereinbefore. This leading end portion 123 is the portion, in which it establishes an overlapping portion 301 together with an outer side cover portion 173 (as will be detailed below). In the metal shell 121, the leading end portion 123, which establishes (or is scheduled to establish) the overlapping portion 301 together with the protector 151, is formed to have a larger-diameter portion 303 (having an external diameter of 12.15 mm) and a smaller-diameter portion 305 (having an external diameter of 12.03 mm), which is located at a position on the trailing end side of that larger-diameter portion 303 and on the leading end side of the mounting thread 129 and which has a smaller diameter than that of the larger-diameter portion 303, to thereby provide a two-step structure.

This metal shell 121 holds the gas detecting element 103 in a coaxial shape such that the leading end portion 105 of the gas detecting element 103 protrudes from the leading end face of the metal shell 121. Specifically, a first plate packing 133 is arranged on the shelf portion 125 of the metal shell 121, as shown in FIG. 1. On the first plate packing 133, moreover, a first fixing member 135 (made of alumina) of a cylindrical shape is arranged having a stepped portion 136 on its inner circumference. The gas detecting element 103 is inserted into the first fixing member 135 so that its engaging flange portion 111 engages with the stepped portion 136 of the first fixing member 135 through a second plate packing 137. A packaged filling layer 139 filled with packed talc is arranged on the trailing end side of the first fixing member 135 and in the clearance which is formed by the outer circumference of the gas detecting element 103 and the inner circumference of the metal shell 121.

On the trailing end side of the packed filling layer 139, moreover, a second fixing member 141 (made of alumina) of a cylindrical shape is arranged, in which the gas detecting element 103 extends therethrough. An additional fastening ring 145 is arranged on the trailing end side of the second fixing member 141 and fastens the trailing end portion of the metal shell 121 additionally radially inward, so that the gas detecting element 103 is held gas-tight in the metal shell 121.

The protector 151 is formed into a dual structure having an inner cover portion 153 of a cylindrical shape for covering the leading end portion 105 of the gas detecting element 103 through a clearance, and an outer cover portion 173 of a cylindrical shape arranged on the outer circumference of the inner cover portion 153.

Of these, the outer cover portion 173 is made of SUS310S having a thickness of 0.5 mm, and is composed of an outer cylindrical portion 175 having an outer diameter of 13.15 mm, and an outer bottom portion 177 positioned on the leading end side of the outer cylindrical portion 175. In this outer cylindrical portion 175, six outer gas communication ports 176 are formed, which can introduce the exhaust gas from the outside into the outer cover portion 175. The outer gas communication ports 176 are individually formed to have elliptical shapes equidistantly in the circumferential direction at positions on the leading end side of the center, as seen in the direction of the axis C. On the other hand, the outer bottom portion 177 is provided at its center with an outer leading end communication port 179 having a circular shape and communicating with the leading end outside of the protector 151.

The inner cover portion 153 is made of SUS310S having a thickness of 0.3 mm, and is composed of an inner cylindrical portion 155 having an external diameter of 8.50 mm, and the inner bottom portion 175 positioned on the leading end side of the inner cylindrical portion 155. The inner cylindrical portion 155 does not have any gas communication ports unlike the outer cylindrical portion 175. On the other hand, an inner bottom portion 157 is provided at its center with an inner leading end communication port 159 having a circular shape and linking to the outside in the leading end direction of the protector 151.

As shown in FIG. 2 and FIG. 3, moreover, the protector 151 is provided with a shielding portion 181 for shielding an inter-cover space 171 intermittently on the trailing end side of the outer gas communication ports 176 as defined between the inner cylindrical portion 155 of the inner cover portion 153 and the outer cylindrical portion 175 of the outer cover portion 173. The shielding portion 181 of this embodiment is composed of six flange portions 183, which protrude radially outward from the trailing end of the inner cylindrical portion 155. Here, the ratio of the area (i.e., the protected area at the time when the shielding portion 181 is projected in the axial direction) of the shielding portions 181 to the opening area of the outer gas communication ports 176 is set to about 30%. These flange portions 183 are provided with six leg portions 185, which radially protrude to the trailing end from the radially outer ends of the flange portions 183.

The inner cover portion 153 and the outer cover portion 173 are fixed to each other at the inner bottom portion 157 and the outer bottom portion 177 through a clearance of about 0.1 mm by partially spot-welding them at four portions of the peripheral portion 157W of the inner leading end communication port 159 and the peripheral portion 177W of the outer leading end communication port 179. As a result, communication is established between the inner leading end communication port 159 and the outer leading end communication port 179.

In this protector 151, as shown in FIG. 2, a trailing end portion 180 of the outer cover portion 173 (i.e., the trailing end portion of the outer cylindrical portion 175) is press-fitted in the larger-diameter portion 303 of the leading end portion 123 of the metal shell 121 and is laser-welded through an annular clearance S to the smaller-diameter portion 305 of the same leading end portion 123.

The fixing structure of the protector 151 and the metal shell 121 constitutes a characteristic feature of the invention and will be described in more detail.

In the metal shell 121, the leading end portion 123, which forms the overlapping portion 301 between itself and the trailing end portion 180 of the outer cover portion 173 of the protector 151, has the aforementioned larger-diameter portion 303 and the smaller-diameter portion 305, and the outer cover portion 173 is fitted (or press-fitted in this embodiment) in the larger-diameter portion 303. Moreover, the outer cover portion 173 forms the annular space S between its own inner circumference and the outer circumference of the smaller-diameter portion 303, and a welded portion W extends in the circumferential direction of the outer cover portion 173 by the laser-weld through the annular space S. In short, the protector 151 (i.e., the outer cover portion 173) and the metal shell 121 are fixed by the press-fit and laser weld. Moreover, the leg portions 185 linking to the shielding portions 181 abut against the leading end faces 123ST of the leading end portion 123 of the metal shell 121. In the gas sensor 101 of this embodiment, the portion, in which the larger-diameter portion 303 and the outer cover portion 173 fit on each other, forms a fitting portion 501, and the portion, in which the smaller-diameter portion 303 and the outer cover portion 173 overlap each other through the annular space S, forms a space-forming portion 503.

Figure 4A:
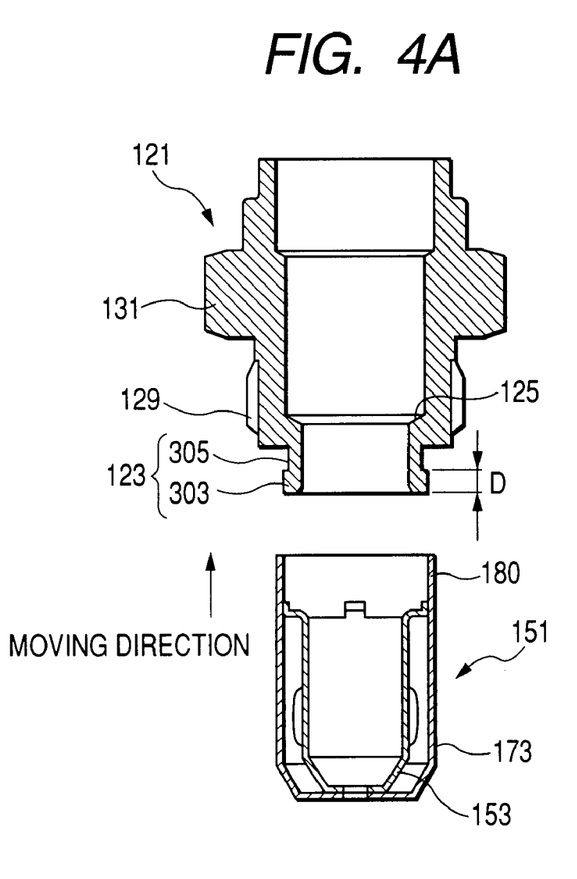
FIG. 4A is an explanatory view showing the manner in which the protector is mounted around the leading end portion of the metal shell.

In the gas sensor 101 of this embodiment, the annular space S has a width T in a radial direction of 0.06 mm. In order to make the positioning proper by the fitting (or the press-fitting) of the outer cover portion 173 and the larger-diameter portion 303 of the metal shell 121, moreover, the length of the fitting portion 501 in the direction of the axis C, that is, the length D (as shown in FIG. 4) from the leading end edge to the trailing end edge of the larger-diameter portion 303 in the direction of the axis C is set to 1 mm.

As a result, the leading end portion 123, the outer cylindrical portion 175 and the inner cylindrical portion 155 of the metal shell 121 construct an inner gas introduction passage 191 for introducing the gas (i.e., the exhaust gas) to be measured, as introduced from the outer gas communication port 176 into the clearance between the inner cover portion 153 and the leading end portion 105 of the gas detecting element 103. More specifically, the inner gas introduction passage 191 guides the measured gas, as introduced from the outer gas communication port 176, to the trailing end side through a space between the outer cylindrical portion 175 and the inner cylindrical portion 155. After this, the exhaust gas is directed to flow over the trailing end of the inner cylindrical portion 155 on the leading end side, as viewed in the direction of the axis C, of an inner circumference side end edge 123ST of a joining face (or the leading end face) of the leading end portion 123 of the metal shell 121 which joins the inner circumference and the outer circumference. Then, the measured gas is guided into the clearance between the inner cover portion 153 and the leading end portion 105 of the gas detecting element 103 and is discharged to the outside of the protector 151 via the inner leading end communication port 159 and the outer leading end communication port 179.

Reverting to FIG. 1, in the metal shell 121, a leading end portion 201S of a metallic outer cylinder 201 of a cylindrical shape is fixed by laser-welding to the whole circumference of the trailing end side of the hexagonal flange portion 131. A grommet 203 made of fluorine rubber is fitted in a trailing end side opening 201K of the metallic outer cylinder 201, and is fixed gas-tight in the metallic outer cylinder 201 by additionally fastening the metallic outer cylinder 201 radially inward. In the central portion of the grommet 203, a through hole is formed, in which a filter member 205 is arranged for introducing the ambient air into the inside of the metallic outer cylinder 201 while preventing intrusion of moisture. On the leading end side of the grommet 203, a separator 207 is arranged, which is made of insulating alumina. Through the grommet 203 and the separator 207, sensor output lead wires 211 and 212 and heater lead wires 213 and a second one not illustrated are arranged. In the separator 207, the connector portions 215B and 216B of first and second terminal fixtures 215 and 216 and heater terminal fixtures 217 and 218 are arranged so as to be insulated from each other. Moreover, the trailing end side of the ceramic heater 109 is housed in the separator 207.

In the first sensor terminal fixture 215, the connector portion 215B is additionally fastened to grip the sensor output lead wire 211 so that it is electrically connected with the same, and an inserted portion 215C is inserted into the bottomed hole of the gas detecting element 103 so that it is electrically connected with the internal electrode layer 108. In the second sensor terminal fixture 216, moreover, the connector portion 216B is additionally fastened to grip the sensor output lead wire 212 so that it is electrically connected with the same, and a grip portion 216C grips the outer circumference near the trailing end of the gas detecting element 103 so that it is electrically connected with the external electrode layer 106. Moreover, the two heater terminal fixtures 217 and a second one not illustrated are individually electrically connected with the heater lead wires 213 and a second one not shown (because FIG. 1 presents a sectional view), and are jointed to a pair of electrode pad portions 109B of the ceramic heater 109 so that they are individually electrically connected.

The separator 207 is provided with a flange portion 207C, which protrude radially outward, and the metallic outer cylinder 201 is provided with four inner protrusions 201C equidistantly along the circumferential direction. By biasing the flange portion 207C backward with a bias member 219 while the trailing end face of the flange portions 207C abutting against the inner protrusions 201C, moreover, the separator 207 is held in the metallic outer cylinder 201. Here, the bias member 219 is formed in a cylindrical shape and is held in the separator 207 by its own elastic force. As the metallic outer cylinder 201 positioned on the radially outer side of the bias member 219 is additionally fastened radially inward, the bias member 219 is deformed to bias the flange portion 207C of the separator 207 backward.

This gas sensor 101 is manufactured by the following process.

At first, a steel material made of SUS430 is subjected to plastic working or cutting working to form the cylindrical metal shell 121 including the hexagonal flange portion 131, the mounting thread 129, the shelf portion and the leading end portion 123. At this time, the metal shell 121 is so shaped that the larger-diameter portion 303 and the smaller-diameter portion 305 positioned on the trailing end side of the larger-diameter portion 303 and having a smaller external diameter may be formed at the leading end portion 123 which is scheduled to form the overlapping portion 301 between itself and the protector 151 (or the outer cover portion 173).

Then, a predetermined amount of lubricant is applied to the surface of the metal shell 121, A lubricant applying method is described in this embodiment. At the time of shaping (e.g., plastic working or cutting working) the aforementioned metal shell 121, the lubricant is employed for lubricating or cooling purposes, and the residual lubricant is applied to the surface of the metal shell 121 shaped. Therefore, the metal shell 121 having the residual lubricant is dipped in a degreasing liquid and is then rinsed with water so that the metal shell 121 is completely cleared of the residual lubricant. Then, the rinsed metal shell 121 is dipped in a lubricant liquid (e.g., an aqueous solution containing about 30% of alkylamine oxide), in which a water-soluble lubricant is dissolved in water, and is then dried to obtain the metal shell 121 having the lubricant newly adhered to its own surface. By suitably adjusting the concentration of the lubricant liquid, a predetermined amount of lubricant can be applied to the surface of the metal shell 121. Thus, the metal shell 121 is prepared, in which the lubricant is applied to the surface including the leading end portion 123.

On the other hand, the outer cover portion 173 and the inner cover portion 153 are prepared, which are formed of SUS310 in advance to a predetermined size to form the bottomed cylindrical shape. Then, the peripheral portion 157W of the inner leading end communication port 159 and the peripheral portion 177W of the outer leading end communication port 179 are spot-welded at four portions to fix the inner cover portion 153 and the outer cover portion 173 coaxially thereby to provide the protector 151.

As shown in FIG. 4A, the protector 151 is moved so far from the leading end side of the metal shell 121 that the trailing end of the outer cover portion 173 abuts against the leading end face of the mounting thread 129. As a result, the trailing end portion of the outer cover portion 173 is mounted around the leading end portion 123 of the metal shell 121. At this time, the outer cover portion 173 is fitted (or press-fitted in this embodiment) on the larger-diameter portion 303 of the leading end portion 123 of the metal shell 121. This press-fitting operation can be smoothly done because the surface of the metal shell 121 wears the lubricant. Moreover, the protector 151 is moved (or press-fitted) far till the trailing end of the outer cover portion 173 abuts against the leading end face of the mounting thread 129, so that the annular space S is formed between the smaller-diameter portion 305 of the leading end portion 123 and the outer cover portion 173. Here in this embodiment, the external diameter of the smaller-diameter portion 305 of the metal shell 121 is adjusted at the shaping time so that the annular space S may have the width T in a radial direction of 0.06 mm. As a result, there are formed the fitting portion 501, in which the larger-diameter portion 303 and the outer cover portion 173 fit on each other, and the space-forming portion 503, in which the smaller-diameter portion 305 and the outer cover portion 173 overlap each other through the annular space S.

Figure 4B:
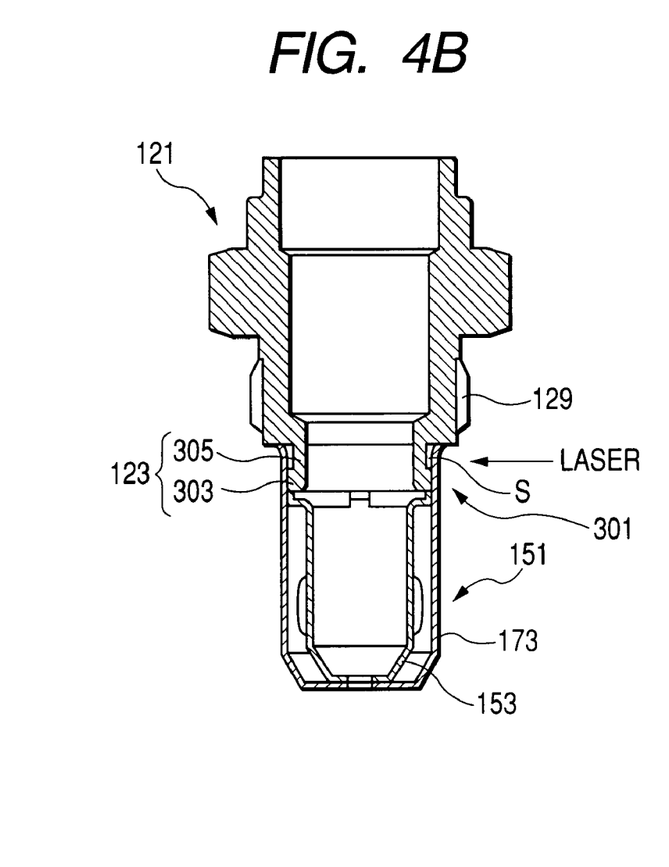
FIG. 4B is an explanatory view showing the manner, in which the smaller-diameter portion of the metal shell and the outer cover portion of the protector are laser-welded.

Next, as shown in FIG. 4B, the outer cover portion 173, which is positioned on the radially outer side of the smaller-diameter portion 305 of the metal shell 121, is irradiated on its outer circumference with a laser beam to form the welded portion W around the entire circumference through the annular space S to thereby laser-weld the protector 151 and the metal shell 121. As a result, the protector 151 and the metal shell 121 are firmly fixed by the press-fitting and the laser-welding.

At this welding step, the lubricant is left on the surface of the smaller-diameter portion 305 of the metal shell 121 so that the lubricant component is gasified by the heat input resulting from the laser welding. In this embodiment, however, the laser welding is executed through the annular space S so that the gas of the lubricant component escapes to the outside from the trailing end side of the outer cover portion 173. As a result, the welded portion W is protected from welding defects such as blow holes due to gas generation so that the welded portion W is stabilized. In this embodiment, the trailing end of the outer cover portion 173 is brought into abutment against the leading end face of the mounting thread 129 of the metal shell 121. Nevertheless, this abutting portion never fails to have more or less of a fine clearance (of about 0.03 mm), so that the trailing end side of the outer cover portion 173 can be degasified.

Into the metal shell 121 having the protector 151 fixed thereon, there are inserted the first plate packing 133, the first fixing member 135, the second plate packing 137, the gas detecting element 103, the talc ring for the packed filling layer 139, the second fixing member 141 and the additional fastening ring 145 sequentially in the recited order. After this, the trailing end portion 132 of the metal shell 121 is additionally fastened radially inward to compress and pack the talc ring to thereby form the packed filling layer 139 and to hold the gas detecting element 103 in the metal shell 121, thus preparing a lower assembly (as shown in FIG. 5).

Next, the sensor output lead wires 211 and 212 and the heater lead wires 213 and a second one not illustrated are individually connected with the first and second terminal fixtures 215 and 216 and the two heater terminal fixtures 217 and a second one not illustrated. While the ceramic heater 109 is being positioned in the first sensor terminal fixtures 215 and 216, the individual lead wires 211, 212 and 213 and a remaining one not illustrated are inserted into the separator 207. Here, the bias member 219 is mounted in advance around the leading end side of the flange portion 207C of the separator 207. The separator 207 thus having the lead wires 211, 212, 213 and one not illustrated therein is inserted into the metallic outer cylinder 201. Next, the individual lead wires 211, 212, 213 and one not illustrated are inserted into the lead wire holes formed in the grommet 203, and this grommet 203 is fitted in the trailing end opening 201K. As a result, an upper assembly 402 is prepared (as shown in FIG. 5).

Figure 5:
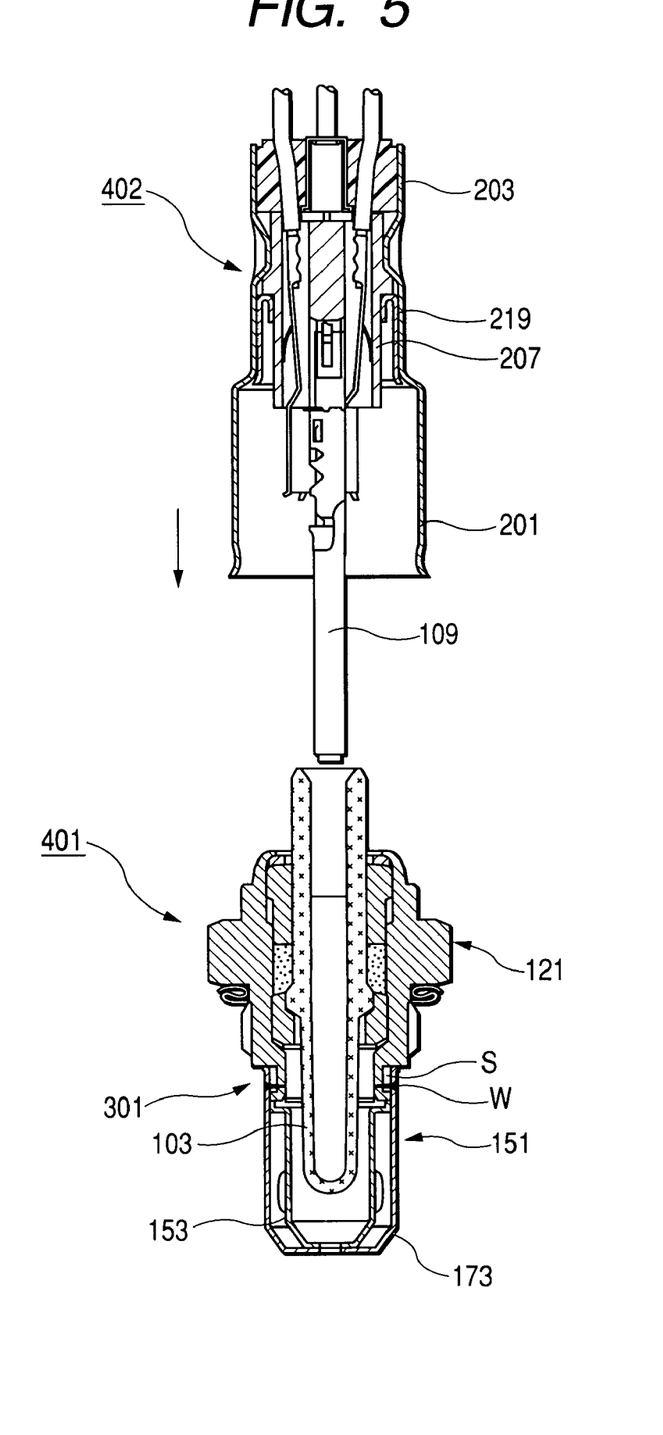
FIG. 5 is an explanatory view showing the manner, in which an upper assembly is assembled with a lower assembly in a state in which the a gas detecting element is held in the metal shell.

As shown in FIG. 5, the upper assembly 402 is moved so far toward the lower assembly 401 that the leading end portion 201S of the metallic outer cylinder 201 comes into abutment against the hexagonal flange portion 131 of the metal shell 121. At this time, the beater 109 is inserted into the gas detecting element 103. After this, the leading end portion 201S of the metallic outer cylinder 201 and the metal shell 121 positioned on the inner side of the outer cylinder 201 are additionally fastened, while pushing the metallic outer cylinder 201, by the fastening jig to tentatively connect them.

Referring to the metallic outer cylinder 201, the portion positioned on the radially outer side is then fastened radially inward to clamp the flange portion 207C of the separator 207 between the bias member 219 and the inner protrusions 201C while deforming the bias member 219. As a result, the separator 207 is held in the metallic outer cylinder 201. Referring to the metallic outer cylinder 201, the portion positioned radially outside of the grommet 203 is additionally fastened radially inward to fix the grommet 203 in a gas-tight state in the metallic outer cylinder 201. Then, the gas sensor 101 is completed by laser-welding the leading end portion 201S of the metallic outer cylinder 201 and the metal shell 121, which have already been tentatively connected, over its entire circumference.

SECOND EMBODIMENT

Next, a gas sensor 601 of the second embodiment of the invention is described. An characteristic portion of the gas sensor 601 is shown in section in FIG. 6. Like the gas sensor 101 of the aforementioned first embodiment, this gas sensor 601 is an oxygen sensor for detecting the oxygen concentration in exhaust gas, but is different in the structure of the mounting portion of the leading end portion 123 of the metal shell 121 and the protector 151 (i.e., the outer cover portion 173). In the following, therefore, the description is centered on portions different from those of the gas sensor 101 of the first embodiment. However, a description of similar portions is omitted or simplified by designating them by common symbols and reference numerals.

Figure 6:
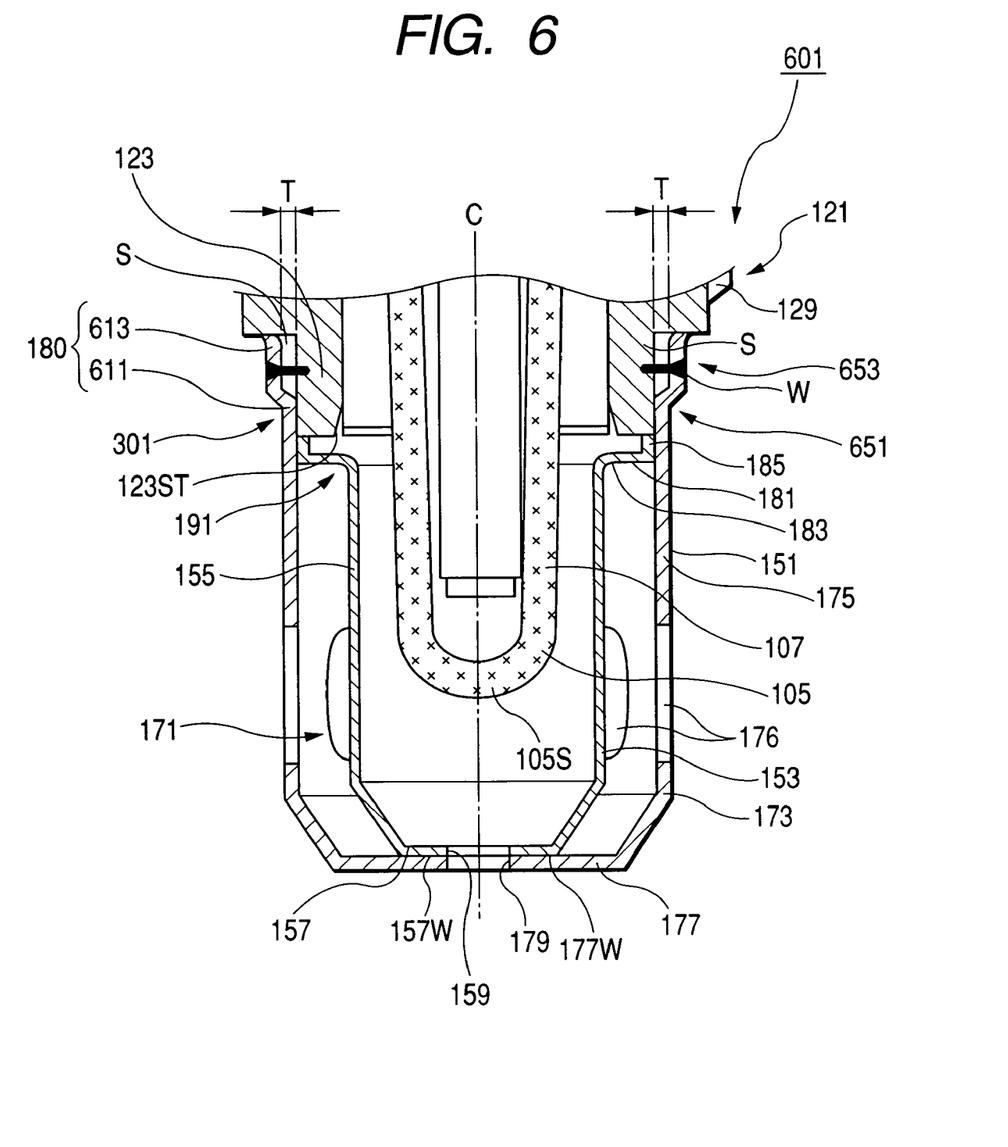
FIG. 6 is a sectional view showing a fixing structure between the protector and the metal shell according to a second embodiment of the invention.

In the gas sensor 601 of this embodiment, the trailing end portion 180 of the outer cover portion 173 of the protector 151, which forms the overlapping portion 301 between itself and the leading end portion 123 of the metal shell 121, is provided with a protector side smaller-diameter portion 611 and a protector side larger-diameter portion 613 having a larger internal diameter than that of the protector side smaller-diameter portion 611. Moreover, the leading end portion 123 of the metal shell 121 does not have the larger-diameter portion 303 and the smaller-diameter portion 305 unlike the aforementioned first embodiment but is made substantially identical in external diameter.

The protector side smaller-diameter portion 611 of the outer cover portion 173 is fitted (or press-fitted in this embodiment) in the leading end portion of the metal shell 121, and an annular space S is formed between the inner circumference of the protector side larger-diameter portion 613 and the outer circumference of the leading end portion 123 of the metal shell 121. The laser-welded portion W is formed in the circumferential direction of the outer cover portion 173 so as to extend through the annular space S. In the gas sensor 601 of this embodiment, the portion, in which the protector side smaller-diameter portion 611 and the leading end portion of the metal shell 121 overlap each other, forms a fitting portion 651. The portion, in which the protector side larger-diameter portion 613 and the leading end portion 123 of the metal shell 121 overlap each other through the annular space S, forms a space-forming portion 653.

In the gas sensor 601 of this embodiment, the annular space S has a width T in a radial direction of 0.05 mm. In order to make the positioning proper by the fitting (or the press-fitting) of the leading end portion 123 of the metal shell 121 and the protector side smaller-diameter portion 611 of the outer cover portion 173, moreover, the length of the fitting portion 651 in the direction of the axis C from the leading end edge of the protector side smaller-diameter portion 611 to the trailing end edges is 0.8 mm.

This gas sensor 601 is manufactured by the following process.

At first, like the foregoing first embodiment, a steel material made of SUS430 is subjected to plastic working and cutting working to form the cylindrical metal shell 121. Next, a predetermined amount of lubricant is applied to the surface of the metal shell 121. The method for applying the lubricant to the metal shell 121 is similar to that of the first embodiment.

On the other hand, there are prepared the outer cover portion 173 and the inner cover portion 153, which are formed of SUS310S in advance to predetermined sizes so as to have the bottomed cylindrical shapes. At this time, the outer cover portion 173 is formed so that the trailing end portion 180, which is scheduled to form the overlapping portion 301 between itself and the leading end portion 123 of the metal shell 121, may be provided with the protector side smaller-diameter portion 611 and the protector side larger-diameter portion 613 positioned on the trailing end side of the protector side smaller-diameter portion 611 and having a larger internal diameter than that of the protector side smaller-diameter portion 611. Then, the inner cover portion 153 and the outer cover portion 173 are coaxially fixed to provide the protector 151.

The protector 151 is moved from the leading end side of the metal shell 121 so far until the trailing end of the outer cover portion 173 abuts against the leading end face of the mounting thread 129, so that the trailing end portion 180 of the outer cover portion 173 is mounted around the leading end portion 123 of the metal shell 121. At this time, the protector side smaller-diameter portion 611 of the outer cover portion 173 is press-fitted. Nevertheless, this press-fitting operation can be smoothly done because the surface of the metal shell 121 wears the lubricant. Moreover, the protector 151 is moved far until it abuts against the leading end face of the mounting thread 129, so that an annular space S is formed between the leading end portion 123 and the protector side larger-diameter portion 613 of the outer cover portion 173.

Next, the protector side larger-diameter portion 613 of the outer cover portion 173 is irradiated on its outer circumference with a laser beam to form the welded portion W over the entire circumference through the annular space S thereby to laser-weld the protector 151 and the metal shell 121. At this welding step, lubricant is left on the surface of the leading end portion 123 of the metal shell 121 so that the lubricant component is gasified by the heat input resulting from the laser welding. In this embodiment, however, the laser welding is executed through the annular space S so that the gas of the lubricant component escapes to the outside from the trailing end side of the outer cover portion 173. Then, the protector 151 is mounted on the leading end portion 123 of the metal shell 121. After this, the gas sensor 601 is completed by way of the steps similar to those of the first embodiment.

The invention has bee described hereinbefore in connection with its embodiments. Nevertheless, the invention should not be construed as being limited to those embodiments but could naturally be suitably modified without departing from the spirit and scope thereof.

In the foregoing embodiments, for example, the element having the closed leading end 105S is used as the gas detecting element 103 but might be suitably modified in shape according to the detection objective so that a plate-shaped gas detecting element could be used.

In the foregoing embodiments, moreover, at the laser-welding time of the outer cover portion 173 and the smaller-diameter portion 305 of the metal shell 121, the gas of the lubricant concentration in the annular space S is released to the outside from the trailing end of the protector 151 (i.e., the outer cover portion 173), but might also be released from the leading end side of the metal shell 121. Specifically, after the metal shell 121 having a predetermined shape is formed by way of plastic working or cutting working, the larger-diameter portion 303 of the leading end portion 123 is grooved or knurled to form a plurality of continuous recesses from the leading end edge to the root end edge of the larger-diameter portion 303.

Then, the lubricant is applied to the surface of the metal shell 121 having the plural recesses formed in the surface of the larger-diameter portion 303, and the protector 151 is then press-fitted in the aforementioned procedure. The welded portion W is formed by laser-welding to form the smaller-diameter portion 305 and the protector 151 (or the outer cover portion 173) through the annular space S. Even if lubricant is left on the surface of the smaller-diameter portion 305 of the metal shell 121, therefore, the gas of the gasified lubricant component can be released through the annular space S from the trailing end of the protector 151 (or the outer cover portion 173) to the outside. At the same time, the lubricant component gas can be released through the spaces in the plural recesses from the leading end side of the metal shell 121 to the outside. At the welding step of the smaller-diameter portion 305 of the metal shell 121 and the outer cover portion 173, a more reliable degasifying effect can be obtained to form a stably welded portion W.

In the foregoing embodiments, moreover, the smaller-diameter portion 305 is formed on the trailing end side of the larger-diameter portion while the larger-diameter portion 303 being formed at the leading end portion 123 of the metal shell 121. Nevertheless, the smaller-diameter portion 305 may be formed on the leading end side of the larger-diameter portion 303. In this modification, the outer cover portion 173 is fitted on the larger-diameter portion 303 so that the annular space S is formed between the smaller-diameter portion 305 and the outer cover portion 173. As a result, the gas of the lubricant component to be produced at the time of forming the welded portion W through the annular space S is released through the annular space S from the leading end side of the protector 151 to the outside.

This application is based on Japanese Patent application JP 2004-66223, filed Mar. 9, 2004, the entire content of which is hereby incorporated by reference, the same as if set forth at length.

What is claimed is:

1. A process for manufacturing a gas sensor, the gas sensor including:
   a gas detecting element extending in an axial direction of said gas sensor in which a leading end side of said gas detecting element is to be exposed to a gas to be measured;

a cylindrical metal shell housing said gas detecting element such that said gas detecting element protrudes from a leading end side of said metal shell;

a cylindrical protector covering an outer circumference of a leading end portion of said metal shell and covering said leading end side of said gas detecting element;

a fitting portion which comprises a portion of said leading end portion of said metal shell and a portion of said protector fitted on each other;

a space-forming portion which comprises a portion of said leading end portion of said metal shell and a portion of said protector overlapping each other through an annular space; and a weld portion welding said protector to said metal shell through said annular space, wherein the annular space has a width in a radial direction of 0.03 mm or more, the process comprising:

applying a lubricant to an outer circumference of said leading end portion of said metal shell;

assembling said metal shell having said lubricant applied thereto and said protector, so that a fitting portion, in which said leading end portion of said metal shell and said protector fit on each other, and a space-forming portion, in which said leading end portion of said metal shell and said protector overlap each other through an annular space, are formed along said axial direction; and welding said metal shell and said protector by forming a welded portion extending from an outer circumference of said protector through said annular space.

2. The process as claimed in claim 1, wherein said leading end portion of said metal shell includes a larger-diameter portion and a smaller-diameter portion having a smaller external diameter than that of said larger-diameter portion, said larger-diameter portion and said protector fit on each other in said fitting portion, and said smaller-diameter portion and said protector overlap each other through said annular space in said space-forming portion.

3. The process as claimed in claim 1, wherein a portion of said protector covering an outer circumference of said leading end portion of said metal shell includes a smaller-diameter portion and a larger-diameter portion having a larger internal diameter than that of said smaller-diameter portion, said smaller-diameter portion and said leading end portion of said metal shell fit on each other in said fitting portion, said larger-diameter portion and said leading end portion of said metal shell overlap each other through said annular space in said space-forming portion.

4. The process as claimed in claim 1, wherein said fitting portion has a length of 0.8 mm or more in said axial direction.

5. The process as claimed in claim 1, wherein said fitting portion is formed by press-fitting said protector on said leading end portion of said metal shell.

6. The process as claimed in claim 1, wherein said welded portion is formed by a laser-welding.

7. The process as claimed in claim 2, wherein at least one recess is formed radially inward in a surface of said larger-diameter portion of said metal shell so as to be continuous from a leading end edge to a trailing end edge of said larger-diameter portion.

8. A gas sensor comprising:

a gas detecting element extending in an axial direction of said gas sensor in which a leading end side of said gas detecting element is to be exposed to a gas to be measured;

a cylindrical metal shell housing said gas detecting element such that said gas detecting element protrudes from a leading end side of said metal shell;

a cylindrical protector covering an outer circumference of a leading end portion of said metal shell and covering the leading end side of said gas detecting element;

a fitting portion which comprises a portion of said leading end portion of said metal shell and a portion of said protector fined on each other;

a space-forming portion which comprises a portion of said leading end portion of said metal shell and a portion of said protector overlapping each other through an annular space; and a weld portion welding said protector to said metal shell through said annular space, wherein the annular space has a width in a radial direction of 0.03 mm or more.

9. The gas sensor as claimed in claim 8, wherein said welded portion extends in a circumferential direction of said gas sensor.

10. The gas sensor as claimed in claim 8, wherein said leading end portion of said metal shell includes a larger-diameter portion and a smaller-diameter portion having an external diameter smaller than that of said larger-diameter portion, said larger-diameter portion and said protector fit on each other in said fitting portion, and said smaller-diameter portion and said protector overlap each other through said annular space in said space-forming portion.

11. The gas sensor as claimed in claim 8, wherein a portion of said protector covering an outer circumference of said leading end portion of said metal shell includes a smaller-diameter portion and a larger-diameter portion having a larger internal diameter than that of said smaller-diameter portion, said smaller-diameter portion and said leading end portion of said metal shell fit on each other in said fitting portion, and said larger-diameter portion and said leading end portion of said metal shell overlap each other in said space-forming portion.

12. The gas sensor as claimed in claim 8, wherein said annular space is partitioned by the weld portion.

13. The gas sensor as claimed in claim 10, wherein the weld portion welds the protector to the small-diameter portion of the metal shell through the annular space.

* * * * *